(12) United States Patent
Burger et al.

(10) Patent No.: US 7,018,651 B2
(45) Date of Patent: Mar. 28, 2006

(54) MOISTURE AND OXYGEN STABLE COMPOSITION AND A PROCESS FOR OBTAINING SAID COMPOSITION

(75) Inventors: Jack Burger, Almere (NL); Fabio Campanile, Amsterdam (NL); Guiseppe Corda, Baarn (NL); Louis Doorn, Zeewolde (NL); Roel Orsel, Huizen (NL); Frans Witteveen, Leusden (NL)

(73) Assignee: Quest International B.V., Naarden (NL)

( * ) Notice: Subject to any disclaimer, the term of this patent is extended or adjusted under 35 U.S.C. 154(b) by 215 days.

(21) Appl. No.: 10/450,662

(22) PCT Filed: Dec. 14, 2001

(86) PCT No.: PCT/NL01/00912

§ 371 (c)(1),
(2), (4) Date: Jun. 16, 2003

(87) PCT Pub. No.: WO02/47492

PCT Pub. Date: Jun. 20, 2002

(65) Prior Publication Data

US 2004/0037890 A1    Feb. 26, 2004

(30) Foreign Application Priority Data

Dec. 15, 2000  (EP)  ................... 00204538

(51) Int. Cl.
*A61K 9/20*   (2006.01)
*A61K 9/16*   (2006.01)
*A61K 9/50*   (2006.01)
*A23L 1/216*  (2006.01)

(52) U.S. Cl. ............. 424/464; 424/464; 424/490; 426/96

(58) Field of Classification Search ............ 424/488, 424/464, 490; 426/96
See application file for complete search history.

(56) References Cited

U.S. PATENT DOCUMENTS

| | | | |
|---|---|---|---|
| 4,534,983 A | | 8/1985 | Koene et al. |
| 4,880,649 A | | 11/1989 | Holzner et al. |
| 5,124,162 A | * | 6/1992 | Boskovic et al. ............ 426/96 |
| 5,573,783 A | * | 11/1996 | Desieno et al. ............ 424/490 |
| 6,056,949 A | | 5/2000 | Menzi et al. |
| 6,482,433 B1 | * | 11/2002 | DeRoos et al. ............ 424/464 |

FOREIGN PATENT DOCUMENTS

| | | |
|---|---|---|
| GB | 844772 | 8/1960 |
| WO | WO 91/17821 | 11/1991 |
| WO | WO 00/36931 | 6/2000 |

\* cited by examiner

Primary Examiner—Carlos A. Azpuru
Assistant Examiner—David Vanik
(74) Attorney, Agent, or Firm—Fitch Even Tabin & Flannery

(57) ABSTRACT

The invention relates to a moisture and oxygen stable composition comprising inert core particles and a partial or complete coating thereon of at least one active compound encapsulated in a carbohydrate matrix, which matrix is characterized by: 5 to 95 wt. % high molecular weight film forming carbohydratre; 5 to 30 wt. % mono, di and trisaccharides; and 0 to 30 wt. % maltodextrin, based on the total weight of the carbohydrate matrix. The active compound to be encapsulated in the carbohydrate matrix can be selected from the group consisting of flavorants, fragrances, pharmaceuticals and wash-active components.

19 Claims, 3 Drawing Sheets

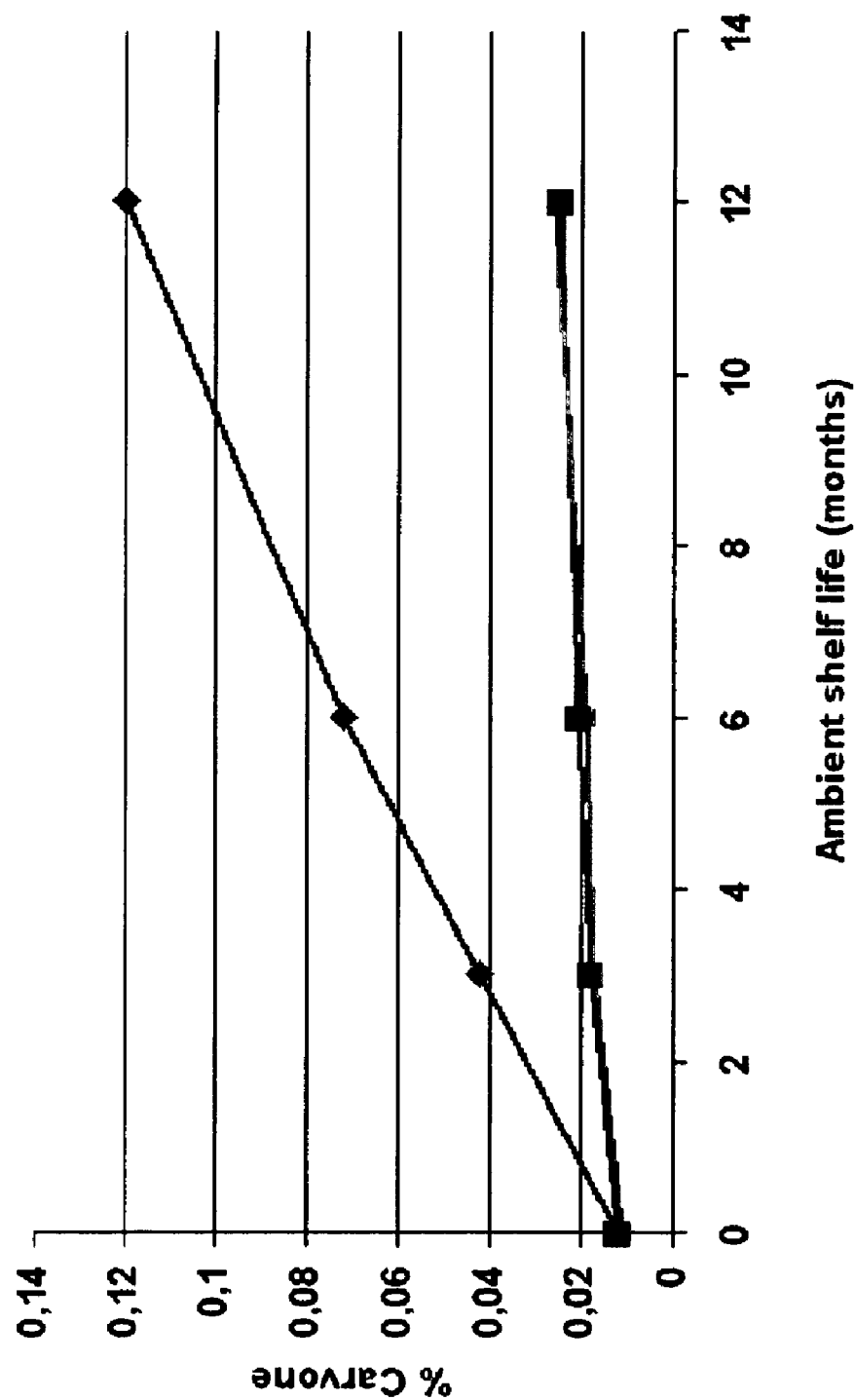

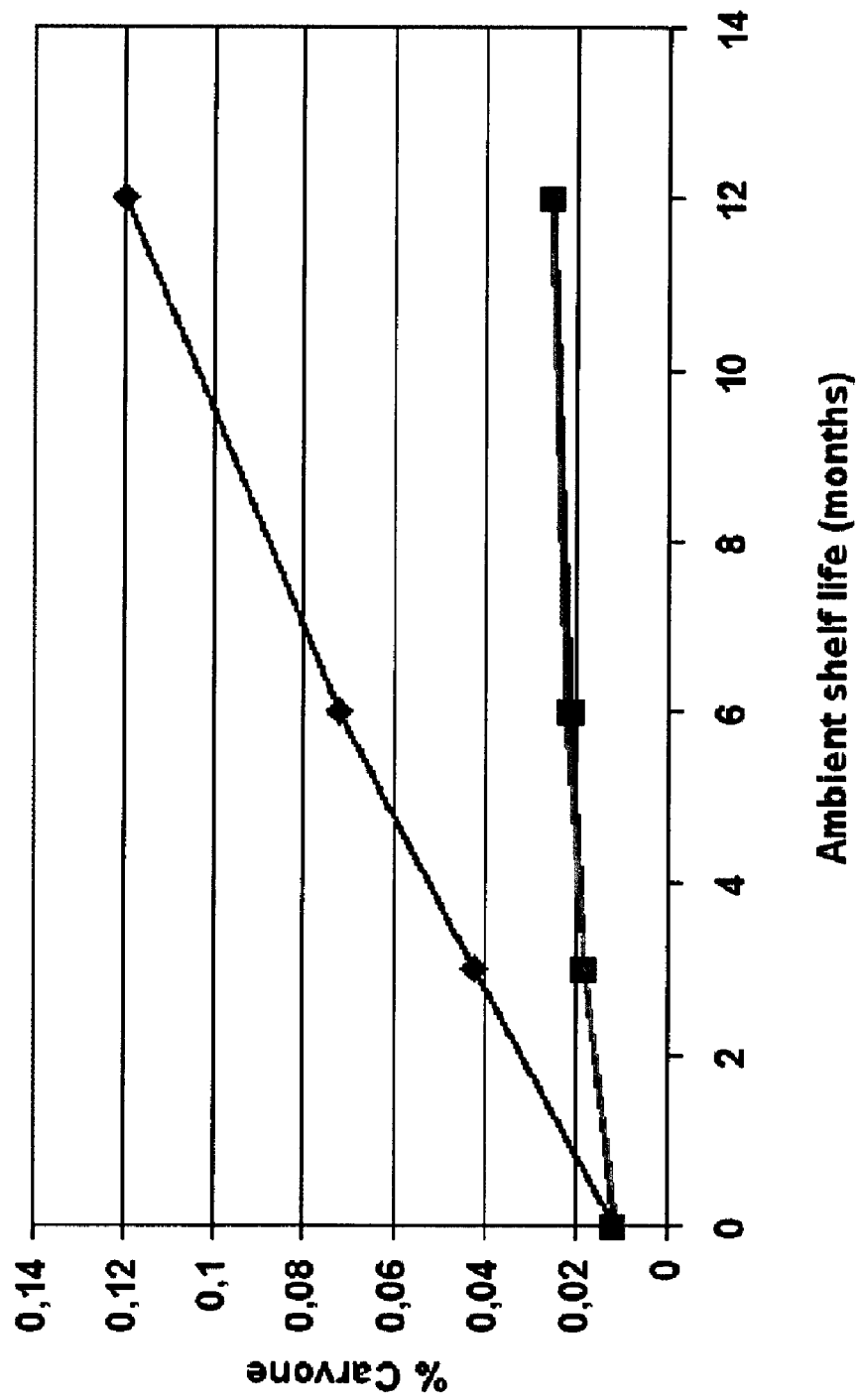

Figure 1:
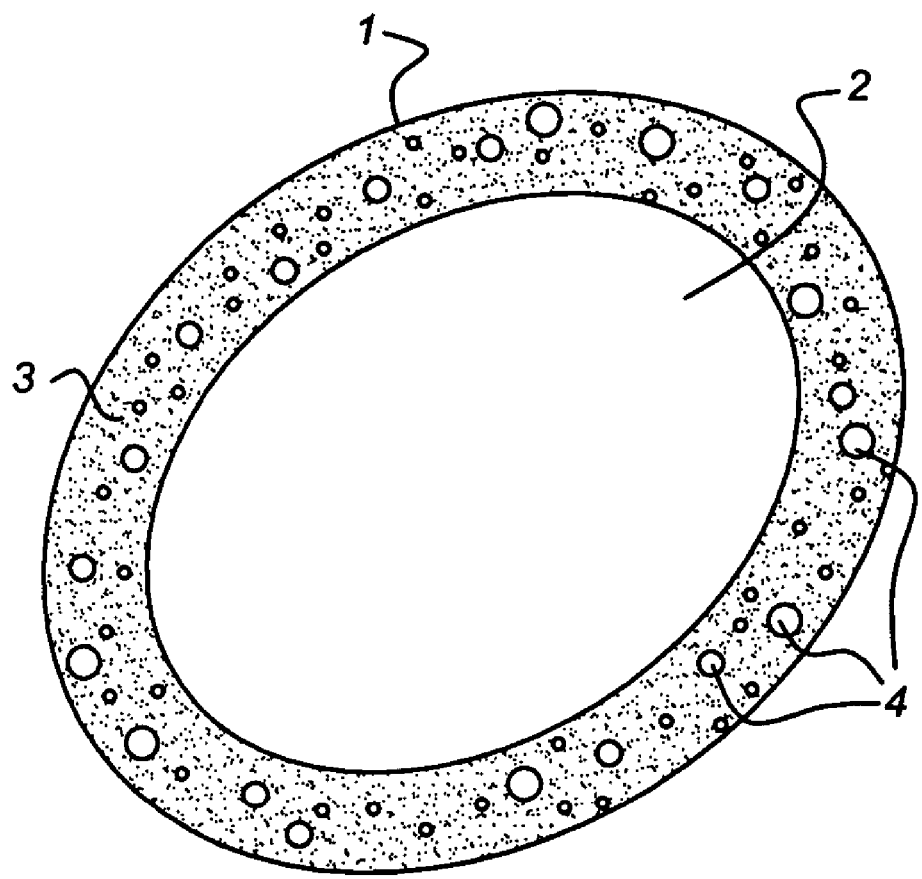

MOISTURE AND OXYGEN STABLE COMPOSITION AND A PROCESS FOR OBTAINING SAID COMPOSITION

CROSS-REFERENCED APPLICATIONS

This application is the National phase of International Application PCT/NL01/00912, the disclosure of which is incorporated herein by reference, filed 14 Dec. 2001, which designated the U.S. and that International Application was published under PCT Article 21(2) in English.

The invention relates to a moisture and oxygen stable composition comprising inert core particles partially or completely coated with at least one active compound like a moisture or oxygen sensitive flavourant, a fragrance or another type of a moisture or oxygen sensitive compound e.g. a pharmaceutical in a carbohydrate matrix. Further, the invention relates to a fluid bed process for fixing volatile flavourants, fragrances or other volatile and moisture or oxygen sensitive compounds in an amorphous carbohydrate matrix as a coating on inert cores.

With regard to the field of flavours it is noted that for instance efforts have been made to give the consumer a fresher tasting reconstitutable beverage mix by using certain natural, natural identical or artificial volatile compounds for improving the consumer's taste perception. Unlike liquid systems which usually retain flavourants without adverse stability problems, dry comestible beverage mixes are often lacking in flavour or have off-flavours due to poor storage stability. A fresh tasting, reconstituted beverage would increase the consumer's perception of freshness which is of paramount importance.

Such compounds as coffee aroma, esters, acetaldehyde, various essential oils and sulphur compounds, augment or enhance the taste perception of convenience foods. Dry comestible mix systems present special problems when one tries to introduce volatile or aromatic flavourants therein. For example, such materials escape through and from the mix, or react so as to degrade or oxidize into compounds which are recognized to be less desirable. Therefore, there has been a long-standing need to fix by encapsulation, and prevent the escape of volatiles within a "powdered-mix" comestible and prevent oxidation thereof. Moreover, the process for fixing a volatile must produce a product which is easily reconstitutable and is capable of holding the fix over prolonged periods and under adverse storage conditions.

A major problem inherent in fixing aromatics in food allowed substrates is the fact that those fixation substrates display idiosyncratic fixation characteristics. The substrate media may be sensitive to moisture, react with the entrained volatile or produce flavour off-notes. Carbohydrates as a class offer a food-acceptable substrate in which volatiles and aromatics have been fixed. However, most water-soluble carbohydrate substrates are hygroscopic and will not reliably hold the fix for long periods. In view of the foregoing, there is a recognized need for an amorphous moisture-stable, water-soluble, food-approved substrate to encapsulate aromatic or volatile flavourants.

Where flavours, such as essential oils, are not protected by an antioxidant, even further problems of off-flavour development are encountered due to oxidation caused by the inability of the carbohydrate matrix to protect the flavour from oxygen.

EP 0 109 698 relates to a process for flavouring dry vegetable material like tea fannings and cut tobacco by separately mixing the dry vegetable material with a microencapsulated flavour and subsequently with an aqueous adhesive solution containing an adhesive like vegetable and microbial gums, for instance gum arabic, starches, cellulose derivatives and saccharides, for instance saccharose, as well as such a quantity of water that the water content of the mixture is at most 5% by weight, based on the total mixture. The obtained dry or almost dry product is subjected, if necessary, to a drying operation respectively a size reduction operation. However, the flavour present in the microcapsules, i.e. droplets of flavour oil encapsulated by an envelope of an edible hydrocolloid such as vegetable gum, a modified starch or gelatin, is not adequately protected against oxidation, so the shelf life of the flavoured products according to EP 0 109 698 is not considered sufficient.

EP 0 070 719 is directed to the encapsulation of a volatile liquid in a carrier material by spraying an aqueous emulsion of the volatile liquid onto solid carrier material particles in a fluidised bed. The volatile liquid may be a flavouring oil or a perfume blend. The aqueous emulsion is prepared by emulsifying the volatile liquid in an aqueous solution of a carrier material selected from modified starches including Capsul®, gum acacia and gelatines. The particles upon which the emulsion is sprayed in the fluidised bed are for instance corn starch particles, spray-dried flavour, gum acacia particles and tea powder. Although the aim of EP 0 070 719 is achieved, i.e. the production of volatile liquid encapsulated particles larger than spray-dried particles, it appeared that at prolonged shelf life, i.e. more than one year, the quality of the encapsulated flavour oil has decreased unsatisfactorily. Further, according to WO 97/16078 the products according to EP 0 070 719 have the disadvantages of an insufficient mechanical stability, rather large amount of dust and a limited flowability.

WO 97/16078 discloses a process for the production of non-dusting, spherical, free flowing, aromatic and odiriferous granulated material by introducing a flavour or fragrance emulsion submers into a fluid bed-rotor granulator comprising fluidised core material having a size in the range of 0.02–3.0 mm. The obtained granulated particles may be subjected to a second coating procedure with, for example, lipid substances. The carrier materials for the emulsion are for instance chemically modified starches, gelatin, gum arabic, carrageenan and other suitable materials. The core particles are selected from carbohydrates like glucose and lactose, fruit powder, fibres like cellulose fibers, sugar alcohols, organic and inorganic salts and herb powders like tea powder. However, at a prolonged shelf life the quality of the encapsulated flavour or fragrance decreases in an undesirable way—as suggested on page 1 of WO 00/36931—undesirable high amounts of flavour are present at the surface of the core particles, and therefore prone to oxidation.

WO 00/36931 relates to encapsulated flavour and/or fragrance preparations having a size of 0.2 up to 2 mm and are produced by spraying an aqueous emulsified flavour and/or fragrance composition into a fluidised bed comprising granulation core particles. The average residence time in the fluidised bed is less than 20 minutes, preferably 5–10 minutes. The obtained fluidised bed granulate product may be encapsulated by a further product like a fat, wax, protein or other product.

EP 0 284 790 B1, discloses the flavouring of all kinds of vegetable products in the form of leaves, powders and particles, for instance tea fannings, by mixing or spraying thereon an emulsion comprising a hydrophobic flavour oil, film forming agent and an emulsifier. The film forming agents are for example polyvinyl acetate, polyvinyl alcohol, (modified) starches, (modified) proteins, gums or all kinds of cellulosic products. The emulsifiers can be selected from fatty acid mono- and diglycerides, esters derived from the combination of fatty acids with sorbitol or a saccharide or their alkoxylated derivatives or an ester of tartaric, citric, ascorbic and lactic acid.

Resuming the above it is brought to the fore that there is a need for an improved moisture and oxygen stable composition comprising an active compound like a flavour oil which composition may lead to products having a prolonged shelf life. This is the more important for commercial products, like flavoured tea fannings in tea bags present in the storage room and later on the shelves of a store.

Surprisingly, it has not been found that an improved moisture and oxygen stable compostion can be obtained by using a carbohydrate matrix comprising an amount of 5 to 95 wt. % high molecular weight film forming carbohydrate in combination with 5 to 30 wt. % mono, di and/or trisaccharides and 0 to 30 wt. % maltodextrin, based on the total weight of the carbohydrate matrix and brought into the form of a glassy state.

Therefore, the invention relates to a moisture and oxygen stable composition comprising inert core particles partially or completely coated with at least one active compound encapsulated in a glassy state carbohydrate matrix, which matrix is characterized by 5 to 95 wt. % high molecular weight film forming carbohydrate;
5 to 30 wt. % mono, di and/or trisaccharides; and
0 to 30 wt. % maltodextrin based on the total weight of the carbohydrate matrix.

More in particular the carbohydrate matrix includes from 45 to 70 wt. %, preferably from 50 to 60 wt. % high molecular weight film forming carbohydrate. Suitable film forming carbohydrates are film forming gums, pectins, alginates, mucilages and mixtures thereof. Preferably the film forming carbohydrates are selected from gum arabic, gum acacia, tragacanth, karaya, ghatti, agar, alginates, carrageenans, fucellan, psyllium and mixtures thereof or from gelatin, dextran, xanthan, curdlan, cellulose, methylcellulose, ethylcellulose, hydroxyethylcellulose, hydroxypropyl cellulose, hydroxypropyl methylcellulose, carboxymethyl cellulose, low methoxy pectin, propylene glycol alginate and mixtures thereof.

Most preferably the film forming agents are film forming gums, hydrocolloids and lipophilically modified starches. Examples of gums are gum arabic and gum acacia. Examples of suitably chemically modified starches are Capsul® and N-Lok (National Starch). Of course, also mixtures of film forming carbohydrates can be used in the compositions according to the invention.

Another component of the carbohydrate matrix according to the invention are the mono, di and trisaccharides, which are used in an amount of 5 to 30 wt. %, preferably 15–25 wt. %, based on the total weight of the carbohydrate matrix. Illustrative examples of mono, di and trisaccharides are glucose, fructose, maltose, sucrose, raffinose, xylitol and materials, having a high content of such sugars like fruit juice solids. Preferably, at least 50 wt. % of the mono, di and trisaccharide material is a disaccharide as a high amount of monosaccharide may result in a somewhat sticky product whereas a high amount of trisaccharide may lead to a product more prone to oxidation. In a preferred embodiment according to the invention the mono, di and trisaccharide material is sucrose.

The carbohydrate matrix according to the invention further includes 0 to 30 wt. %, preferably 10 to 30 wt. % maltodextrin. The maltodextrin will preferably have a dextrose equivalent (DE) in the range of 1 to 25, most preferably in the range of 10 to 20. A variety of maltodextrins meeting the above requirements are readily available commercially, including maltodextrins from e.g. tapioca, maize and potato.

The carbohydrate matrix may be softened by the incorporation of up to 5 wt. % of an edible polyol such as glycerol, preferably 1 to 3 wt. %, based on the carbohydrate matrix. Also other components like anti-foam agents in an amount of up to 0.2% may be added.

The active compound to be encapsulated in the carbohydrate matrix can be selected from the group consisting of flavourants, fragrances, pharmaceuticals and wash-active components.

Flavourants are well-known in the art and are mentioned, e.g., in S. Arctander, Perfume and Flavor Materials of Natural Origin (Elisabeth, N.J., USA, 1996), in T. E. Furia et al, CRC Fenaroli's Handbook of Flavor Ingredients, 2nd Ed. (Cleveland, CRC Press Inc., 1975), and in H. B. Heath, Source Book of Flavors (The Avi Publishing Company Inc., Westport, Conn., 1981).

Fragrances and mixtures thereof which can be used for the preparation of perfumed articles are e.g. naturally occurring products such as essential oils, absolutes, resinoids, resins, concretes etc., natural, nature identical and artificial fragrances, such as hydrocarbons, alcohols, aldehydes, ketones, ethers, acids, esters, acetals, ketals, nitrites etc., covering saturated and unsaturated compounds, aliphatic, carbocyclic and heterocyclic compounds, for instance as disclosed in S. Arctander (loc.cit.).

Examples of flavour and/or fragrance ingredients which may be used within the scope of the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert. butylcyclohexyl acetate, isononyl acetate, vetiveryl acetate, vetiverol, $\alpha$-hexyl-cinnamaldehyde, 2-methyl-3-(p-tert.butylphenyl)-propanal, 2-methyl-3-(p-isopropyl phenyl)-propanal, 3-(p-tert.butylphenyl)-propanal, tricyclodecenyl acetate, tricyclo-decenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentyl-cyclopentane, 2-n-heptyl-cyclopentanone, 3-methyl-2-pentyl-2-cyclopentanone, n-decanal, n-dodecanal, dec-9-en-1-ol, phenoxy-ethyl isobyutyrate, phenylacetaldehyde dimethylacetal, phenyl-acetaldehyde diethylacetal, geranyl nitrile, citronellyl nitrile, cedryl acetate, 3-iso-camphyl cyclohexanol, cedrylmethyl ether, isolongifolanone, aubepine nitrile, aubepine, heliotropine, coumarin, eugenol, vanillin, diphenyl oxide, hydroxy citronellal, ionones, methyl ionones, isomethyl ionones, irones, cis-3-hexenol and esters thereof, indan musk fragrances, tetralin musk fragrances, isochroman musk frangrances, macrocyclic ketones, macrolactone musk fragrances, ethylene brassylate and aromatic nutri-musk frangrances.

The fragrance compositions according to the invention may be used successfully in perfumed articles. Examples of such perfumed articles are: soap, bath products, washing agents, dish washing and cleaning agents, pommanders, candles, cosmetics such as creams, ointments, body deodorant sticks and antiperspirant sticks.

Also pharmaceuticals and wash-active components which are prone to humidity or oxygen can be used as active compound to be encapsulated in the carbohydrate matrix according to the invention.

The inert core particles can be any particulate material which is inert under the fluidised bed conditions. However, for the sake of convenience the inert core particles can be selected from edible materials, preferably from the group consisting of vegetable particles like tea fannings, tea dust and tobacco particles, all kinds of crystal products like sugar crystals and salt crystals, further all sorts of fibers like organic and artificial fibers like gum arabic, cellulose cells, maltodextrin, plant seeds like sesame seed, caraway seed etc. and spray-dried flavours. The core particles may have a size in the range of 0.1–3 mm, preferably 0.2–1.5 mm.

A major application of the invention is related to the field of flavours. In this respect it is noted that the final product according to the invention is capable of protecting and retaining 1 to 40 wt. % or even more, preferably 10 to 20 wt. % flavourant as active compound, depending on the type of flavourant and based on the total weight of the flavour. Examples of flavourants, in particular aromatic or volatile flavourants, to be encapsulated in the carbohydrate matrix according to the invention are for instance essential oils, like bergamot oil, citrus oil, e.g. lemon oil, orange oil, grapefruit oil and other volatile flavourants, like bakery and savoury flavourants as well as food flavourants such as strawberry, raspberry, kiwi, etc. Also other types of active compounds as indicated above can be encapsulated in the carbohydrate matrix according to the invention in an amount of 1–40 wt. % or more, preferably 10–20 wt. %, based on the total weight of the composition.

With respect to the weight ratio between the core particles and the coating it is brought to the fore that said ratio may vary considerably but preferably is in the range of 5.1 up to 1.5, most preferably about 1:1.

The products according to the invention can be produced by any suitable process, according to which a coating is fixed on inert core particles, for instance performed in a tumbler etc. Most preferably, the products according to the invention are produced by means of a fluidised bed process.

Therefore, a further aspect of the inventin is embodied by a process for producing the moisture and oxygen stable composition, comprising the steps of a) forming an aqueous carbohydrate solution containing a carbohydrate mixture consisting of 5 to 95 wt. % high molecular weight folm forming carbohydrate(s), 5 to 30 wt. % mono, di and trisaccharide(s), and 0 to 30 wt. % maltodextrin(s), b) incorporating at least one active compound defined above into the solution of step (a), and c) introducting the aqeous solution of step (b) into a fluidized bed comprising inert core particles and using an inlet air temperature of 40–120° C., preferably 60–100° C., to obtain a stable core product coated with the active compound encapsulated in a glassy state carbohydrate matrix.

More in general, the fluidised bed process may be carried out by spraying an emulsion of active compound and the carbohydrate matrix in water into a fluidised bed agglomerator, which has previously been charged with a quantity of inert core particles or with a sample of small encapsulates containing the carbohydrate matrix to be employed in a bulk preparation. The emulsion containing the carbohydrate matrix coats the inert core particles fluidised by the passage of air through the bed and causes some agglomeration of the particles and a build-up of the components of the emulsion including the carbohydrate matrix. Since the residence time in the fluidised bed is controllable, the spraying of the emulsion may be continued until the required particle size of encapsulate has been obtained.

In commercial practice, it is desirable to run the process as a continuous one, using equipment of appropriate size for the production required. Such continuous running tends to ensure the maximum uniformity of product. To achieve this, careful control of input spray rate, fluidisation air-flow rate and its temperature must be exercised.

The fluidised bed apparatus for use in this process can be selected from those of various manufacturers, including Aeromatic AG of Muttenz in Switzerland and "Strea-1" laboratory agglomerator, also supplied by Aeromatic AG. Other useful agglomerators are supplied by the Calmic Division of William Boulton of Burslem, England and by the firm Glatt, Binzen, Germany.

The invention is elucidated by means of the following examples and FIGS. 1–3.

FIG. 1 represents a schematical cross-section of an inert core particle coated with an active compound in a carbohydrate matrix according to the invention. More in particular the symbols 1–4 in FIG. 1 have the following meanings:

1) represents an inert core particle, coated with an active compound in a carbohydrate matrix;
2) represents the inert core;
3) represents the carbohydrate matrix; and
4) represents the active compound.

FIG. 2 illustrates the accelerated shelf life test of
- ♦ a product according to the prior art based on 25 wt. % orange flavourant (QL 06830 marketed by Quest International, the Netherlands) and 75 wt. % of a carbohydrate matrix consisting of 50 wt. % Capsul® and 50 wt. % maltodextrin (DE 20) indicated in Table A, and sprayed at an inlet temperature of 85° C.;
- ■ a product according to the invention based on 25 wt. % orange flavourant (QL 06830) and 75 wt. % of a carbohydrate matrix consisting of 50 wt. % Capsul®, 25 wt. % maltodextrin (DE 20) and 25 wt. % sucrose indicated in Table A and sprayed at an inlet temperature of 85° C., and
- Δ a product according to the invention as indicated above under ■ and sprayed at an inlet temperature of 100° C.

In FIG. 2 the X-axis represents the time in months at ambient (20° C.) temperature, and the Y-axis represents the amount of carvone in wt. %, formed from the compositions according to the prior art and the invention due to oxidation of the limonene component of the used orange flavourant during the accelerated shelf life test at 40° C. and at a relative humidity (RH) of 30%.

FIG. 3 illustrates the accelerated shelf life test of
- ♦ the product according to the prior art defined in the legenda of FIG. 2, applied on a laboratory scale (GPCG01 Wurster)
- ■ a product according to the invention, defined in the legenda of FIG. 2, applied on a laboratory scale (GPCG01 Wurster); and
- Δ a product according to the invention based on 25 wt. % orange flavourant (QL 06830) and 75 wt. % of a carbohydrate matrix consisting of 50 wt. % Capsul®, 25 wt. % maltodextrin (DE 20) and 25 wt. % sucrose applied in Table C on a pilot plant scale (GPCG30 Wurster). All samples were introduced at an inlet temperature of 85° C.

In FIG. 3 the X-axis represents the time in months at ambient (20° C.) temperature, and the Y-axis represents the amount of carvone in wt. %, formed from the compositions according to the prior art and the invention due to oxidation of the limonene component of the used orange flavourant during the accelerated shelf life test at 40° C. and at a relative humidity (RH) of 30%. As apparent from FIG. 3 there is no difference in oxidation stability when using a pilot plant installation (GPCG30 Wurster) or a laboratory installation.

EXAMPLE 1

The following two formulations were prepared by dissolving or dispersing the components indicated below
(a) 500 g of a carbohydrate matrix comprising 50 wt. % (250 g) Capsul® and 50 wt. % (250 g) maltodextrin (DE 20) being a carbohydrate matrix used for marketed products; and
(b) 500 g of a carbohydrate matrix consisting of 50 wt. % (250 g) Capsul®, 25 wt. % (115 g) maltodextrin (DE 20) and 25 wt. % (125 g) sucrose being a carbohydrate matrix according to the invention under stirring in 600 g water of 80° C. for 30 minutes. Then the mixture was cooled to 20° C. An orange flavourant (QL 06830) without any antioxidant preservative was added in an amount of 25 wt. % on total dry solids (166 g) under stirring and the prepared feed was homogenised using a Ultra Turrax T50 at 10,000 rpm for about 3 minutes. The homogenised feed (1266 g) was fed to a fluid bed GPCG01 laboratory agglomeration Wurster equipment with 700 g tea fannings fluidised, using a two fluid nozzle at 2 bar. Inlet air temperature was varied between 50° C. and 105° C., resulting in a variable product temperature between 38 and 55° C. The applied feed temperature was 30° C. and the air inlet flow was 120 m³/hr.

TABLE A

| Experiment | Matrix Flavour Pay load % | Inlet Temp. ° C. | Product Temp. ° C. | Fresh oil retention % | Spray-rate g/min. | residence time Min. |
|---|---|---|---|---|---|---|
| GPCG01 Wurster | (a) QL06830 25% | 85 | 54 | 84 | 52 | 20 |
| GPCG01 Wurster | (b) QL06830 25% | 55 | 40 | 82 | 18 | 60 |
| GPCG01 Wurster | (b) QL06830 25% | 65 | 40 | 87 | 38 | 30 |
| GPCG01 Wurster | (b) QL06830 25% | 75 | 43 | 88 | 50 | 25 |
| GPCG01 Wurster | (b) QL06830 25% | 85 | 58 | 92 | 45 | 31 |
| GPCG01 Wurster | (b) QL06830 25% | 95 | 50 | 94 | 60 | 19 |
| GPCG01 Wurster | (b) QL06830 25% | 100 | 56 | 97 | 60 | 19 |

TABLE A-continued

| Experiment | Matrix Flavour Pay load % | Inlet Temp. ° C. | Product Temp. ° C. | Fresh oil retention % | Spray-rate g/min. | residence time Min. |
|---|---|---|---|---|---|---|
| GPCG01 Wurster | (b) QL06830 25% | 105 | 57 | 92 | 65 | 16 |

As apparent from FIG. 2, the product according to the invention had an excellent stability and a desired long storage life compared to the prior art product. More in particular the storage time of 8 weeks in the accelerated shelf life test at 40° C. and a RH of 30% corresponds to a storage time of about one year at room temperature (20° C.) and a RH of 30%.

EXAMPLE 2

The formulations according to the invention were prepared in the way disclosed in Example 1, provided that the orange flavourant (QL 06830) without any antioxidant preservative was added in the range of 30 to 60 wt. % on total dry matrix solids (i.e. the carbohydrate matrix was used in an amount ranging from 70 to 40 wt. %).

TABLE B

| Experiment | Matrix Flavour Pay load | Inlet Temp. | Product Temp. | Fresh oil retention | Spray-rate | residence time |
|---|---|---|---|---|---|---|
| GPCG01 Wurster | QL06830 30% | 85 | 57 | 88 | 45 | 17 |
| GPCG01 Wurster | QL06830 35% | 85 | 56 | 86 | 45 | 12 |
| GPCG01 Wurster | QL06830 40% | 54 | 36 | n.d.* | 18 | 33 |
| GPCG01 Wurster | QL06830 50% | 52 | 36 | n.d.* | 19 | 27 |
| GPCG01 Wurster | QL06830 60% | 55 | 35 | n.d.* | 19 | 18 |

*n.d. = not determined

The product according to the invention had an excellent stability and a desired long storage life. More in particular the storage time of 8 weeks in the accelerated shelf life test at 40° C. and a RH of 30% corresponds to a storage time of about one year at room temperature (20° C.) and a RH of 30%.

EXAMPLE 3

A formulation according to the invention was prepared in the way disclosed in Example 1, but investigated on pilot plant scale (40 kg scale).

TABLE C

| Experiment | Matrix Flavour Pay load % | Feed Temp. ° C. | Inlet Temp. ° C. | Product Temp. ° C. | Fresh oil retention % | Air m3/hr | Spray-rate g/min. | residence time Min. |
|---|---|---|---|---|---|---|---|---|
| GPCG30 Wurster | QL06830 25% | 30 | 85 | 38 | 90 | 1000 | 650 | 53 |

As apparent from FIG. 3, the product according to the invention had an excellent stability and a desired long storage life. More in particular the storage time of 8 weeks in the accelerated shelf life test at 40° C. and a RH of 30% corresponds to an ambient shelflife of about one year at room temperature (20° C.) and a RH of 30%.

The invention claimed is:

1. A moisture and oxygen stable composition comprising inert core particles partially or completely coated with at least one active compound encapsulated in carbohydrate matrix, which matrix is characterized by
   - 45 to 70 wt. % high molecular weight film forming carbohydrate;
   - 5 to 30 wt. % mono, di and trisaccharides; and
   - 10 to 30 wt. % maltodextrin based on the total weight of the carbohydrate matrix.

2. The composition according to claim 1, characterized in that the film forming carbohydrate is present in an amount of 50–60 wt. % based on the total weight of the carbohydrate matrix.

3. The composition according to claim 1, characterised in that the film forming carbohydrate is selected from the group consisting of gum arabic, gum acacia, lipophilically modified searches and mixtures thereof.

4. The composition according to claim 1 or 3, characterised in that the mono, di and trisaccharides are present in an amount of 15–25 wt. % based on the total weight of the carbohydrate matrix.

5. The composition according to claim 1, characterised in that at least 50 wt. % of the mono, di and trisaccharide material is a disaccharide.

6. The composition according to claim 5, characterised in that the disaccharide is sucrose.

7. The composition according to claim 1, characterised in that the maltodextrin has a dextrose equivalent (DE) in the range of 1 to 25.

8. The composition according to claim 1, characterised in that the active component encapsulated in the carbohydrate matrix is selected from the group consisting of flavourants, fragrances, pharmaceuticals and wash-active components.

9. The composition according to claim 1, characterised in that the encapsulated active compound is at least one flavourant selected from the group consisting of essential oils, like bergamot oil, citrus oil, bakery flavourants and savoury flavourants.

10. The composition according to claim 1, characterised in that the encapsulated active compound is present in an amount of 1–40 wt. % based on the total weight of the active compound containing carbohydrate matrix.

11. The composition according to claim 1, characterised in that the core particles are selected from the group consisting of tea fannings, tea dust, tobacco particles, sugar crystals, salt crystals, plant seeds, fibres, spray-dried particles and cellulose cells.

12. The composition according to claim 1, characterised in that the core particles have a size in the range of 0.1–3 mm.

13. The composition according to claim 1, characterised in that the weigh ratio of the core particles and the coating is from 5:1 to 1:5.

14. A process for producing a moisture and oxygen stable composition comprising the steps of
   (a) forming an aqueous carbohydrate solution containing a carbohydrate mixture consisting of 45 to 70 wt. % high molecular weight film forming carbohydrate(s), 5 to 30 wt. % mono, di and trisaccharide(s), and 10 to 30 wt. % maltodextrin(s), wherein the wt. % is based on the total weight of the carbohydrate matrix;
   (b) incorporating at least one active compound into the solution of step (a); and
   (c) introducing the aqueous solution of step (b) into a fluid bed comprising inert core particles and using an inlet air temperature of 40–120° C., preferably 60–100° C., to obtain a stable core product coated with the active compound encapsulated in a carbohydrate matrix.

15. The process according to claim 14, characterised in that the active compound is selected from the group consisting of flavourants, fragrances, pharmaceuticals and wash-active components.

16. The process according to claim 14 or 15, characterized in that the core particles are selected from the group consisting of tea fannings, tobacco particles, sugar crystals, salt crystals plant seeds, fibres, spray-dried particles and cellulose cells.

17. Products comprising the composition prepared by the process according to claim 5.

18. The composition according to claim 1, wherein the maltodextrin has a dextrose equivalent (DE) in the range of 10 to 20.

19. The composition according to claim 1, characterized in that the composition is oxygen and moisture stable for a period of time corresponding to an ambient shelf life of about 1 year at 20% and relative humidity of 30%.

* * * * *